(12) United States Patent
Trout, III et al.

(10) Patent No.: US 6,648,912 B2
(45) Date of Patent: Nov. 18, 2003

(54) TEMPORARY STENT ASSEMBLY FOR USE IN A SURGICAL PROCEDURE

(75) Inventors: Hugh H. Trout, III, Washington, DC (US); Howard M. Tanner, Logan, UT (US); Frank Patterson, Exeter, NH (US)

(73) Assignee: Eva Corporation, Bethesda, MD (US)

( * ) Notice: Subject to any disclaimer, the term of this patent is extended or adjusted under 35 U.S.C. 154(b) by 55 days.

(21) Appl. No.: 09/783,205

(22) Filed: Feb. 15, 2001

(65) Prior Publication Data

US 2002/0038144 A1 Mar. 28, 2002

Related U.S. Application Data

(60) Provisional application No. 60/182,541, filed on Feb. 15, 2000.

(51) Int. Cl.[7] .............................. A61F 2/06; A61M 29/00
(52) U.S. Cl. ...................... 623/1.15; 623/1.11; 606/113; 606/194; 606/198
(58) Field of Search ............................... 623/1.11, 1.12, 623/1.13, 1.14, 1.15; 606/194, 113, 198

(56) References Cited

U.S. PATENT DOCUMENTS

| | | | | |
|---|---|---|---|---|
| 4,140,126 A | * | 2/1979 | Choudhury | 606/194 |
| 5,098,440 A | * | 3/1992 | Hillstead | 606/113 |
| 5,201,741 A | * | 4/1993 | Dulebohn | 606/113 |
| 5,509,900 A | * | 4/1996 | Kirkman | 606/198 |
| 5,749,890 A | * | 5/1998 | Shaknovich | 606/198 |
| 5,938,696 A | | 8/1999 | Goicoechea et al. | |
| 6,090,115 A | * | 7/2000 | Beyar et al. | 606/113 |
| 6,120,535 A | * | 9/2000 | McDonald et al. | 623/1.39 |
| 6,162,237 A | * | 12/2000 | Chan | 606/198 |
| 6,187,015 B1 | * | 2/2001 | Brenneman | 606/108 |
| 6,348,067 B1 | * | 2/2002 | Baum et al. | 623/1.19 |
| 6,383,171 B1 | * | 5/2002 | Gifford et al. | 623/1.13 |
| 2002/0074004 A1 | * | 6/2002 | Boyd et al. | 128/898 |

* cited by examiner

*Primary Examiner*—Rodney M. Lindsey
(74) *Attorney, Agent, or Firm*—Collier Shannon Scott, PLLC; John N. Coulby; Adriana L. Zachousky

(57) ABSTRACT

The present invention is directed to a stent assembly for use in temporarily securing a surgical component during a surgical procedure. The stent assembly includes a catheter assembly having at least one primary passageway extending there through. The stent assembly further includes a securing assembly for exerting a force against the surgical component for temporarily securing the surgical component during the surgical procedure. The securing assembly includes a portion that extends through the at least one primary passageway. The catheter assembly may include a secondary passageway. The secondary passageway is adapted to receive a guide device therein. The securing assembly has a retracted position and an extended position. The securing assembly exerts a force against the surgical component while the securing means is in the extended position. The securing assembly may contain a coating which increases the gripping force of the securing assembly.

20 Claims, 5 Drawing Sheets

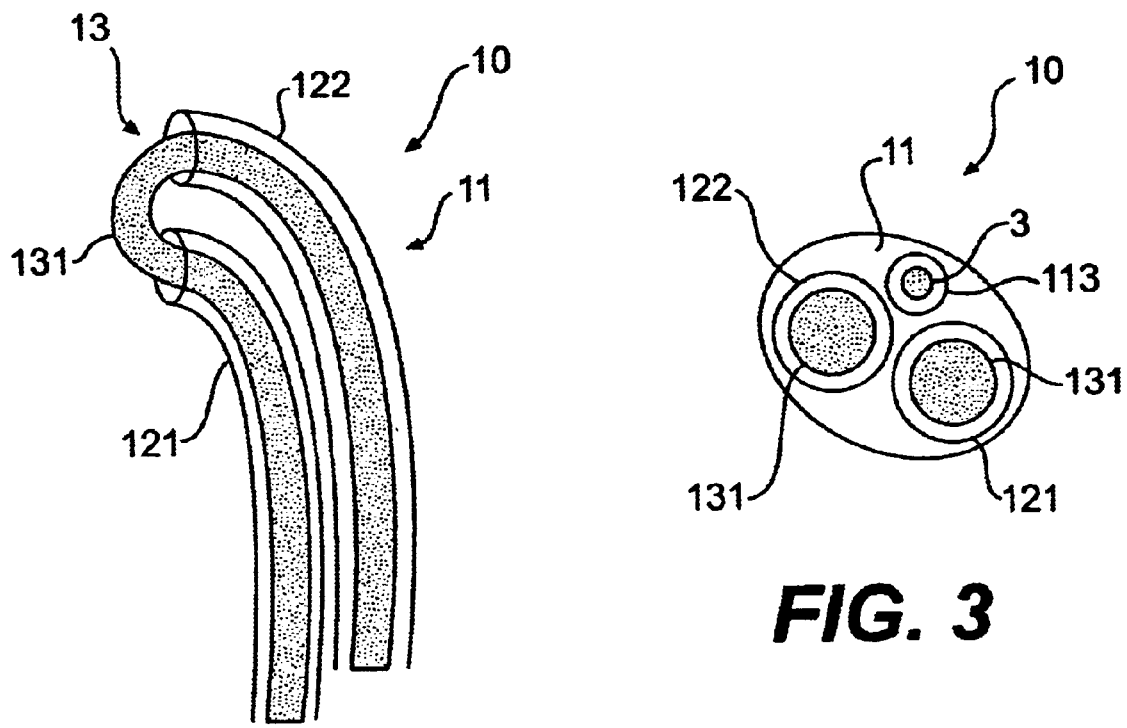
FIG. 2
FIG. 3
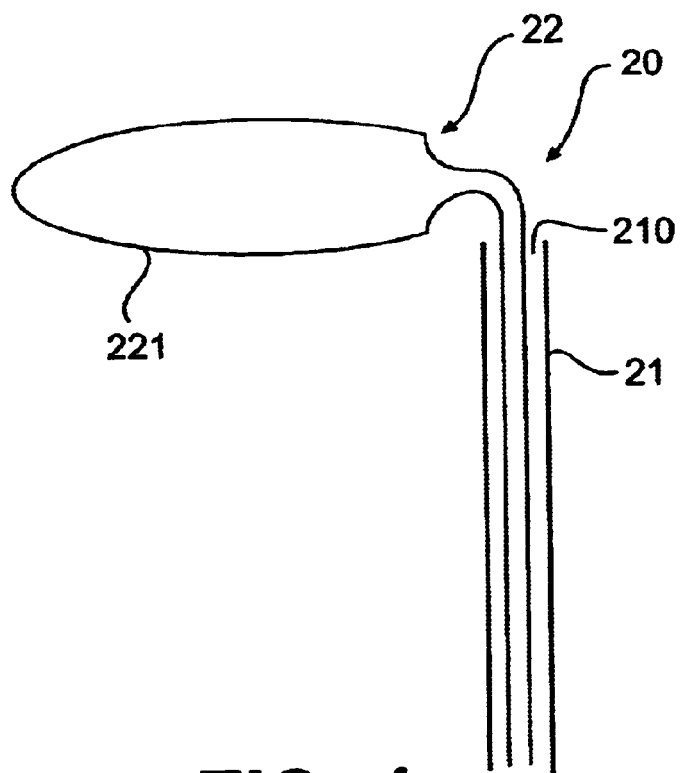
FIG. 4

TEMPORARY STENT ASSEMBLY FOR USE IN A SURGICAL PROCEDURE

CROSS REFERENCE TO RELATED APPLICATIONS

The present invention relates to and claims priority on U.S. Provisional Patent Application Serial No. 60/182,541, filed Feb. 15, 2000.

FIELD OF THE INVENTION

The present invention relates generally to a stent assembly for use during a surgical procedure. In particular, the present invention is directed to a temporary stent assembly for temporarily securing a surgical component during a surgical procedure during the process of permanently securing the surgical component to a vessel.

BACKGROUND OF THE INVENTION

An aneurysm is a ballooning of the wall of an artery resulting from the weakening of the artery due to disease or other conditions. Left untreated, the aneurysm will frequently rupture, resulting in loss of blood through the rupture and death.

Aortic aneurysms are the most common form of arterial aneurysm and are life threatening. The aorta is the main artery which supplies blood to the circulatory system. The aorta arises from the left ventricle of the heart, passes upward and bends over behind the heart, and passes down through the thorax and abdomen. Among other arterial vessels branching off the aorta along its path, the abdominal aorta supplies two side vessels to the kidneys, the renal arteries. Below the level of the renal arteries, the abdominal aorta continues to about the level of the fourth lumbar vertebrae (or the navel), where it divides into the iliac arteries. The iliac arteries, in turn, supply blood to the lower extremities and perineal region.

It is common for an aortic aneurysm to occur in that portion of the abdominal aorta between the renal arteries and the iliac arteries. This portion of the abdominal aorta is particularly susceptible to weakening, resulting in an aortic aneurysm. Such an aneurysm is often located near the iliac arteries. An aortic aneurysm larger than about 5 cm in diameter in this section of the aorta is ominous. Left untreated, the aneurysm may rupture, resulting in rapid, and usually fatal, hemorrhaging. Typically, a surgical procedure is not performed on aneurysms smaller than 5 cm as no statistical benefit exists to do so.

Aneurysms in the abdominal aorta are associated with a particularly high mortality rate; accordingly, current medical standards call for urgent operative repair. Abdominal surgery, however, results in substantial stress to the body. Although the mortality rate for an aortic aneurysm is extremely high, there is also considerable mortality and morbidity associated with open surgical intervention to repair an aortic aneurysm. This intervention involves penetrating the abdominal wall to the location of the aneurysm to reinforce or replace the diseased section of the abdominal wall (i.e., abdominal aorta). A prosthetic device, typically a synthetic tube graft, is used for this purpose. The graft serves to exclude the aneurysm from the circulatory system, thus relieving pressure and stress on the weakened section of the aorta at the aneurysm.

Repair of an aortic aneurysm by surgical means is a major operative procedure. Substantial morbidity accompanies the procedure, resulting in a protracted recovery period. Further, the procedure entails a substantial risk of mortality. While surgical intervention may be indicated and the surgery carries attendant risk, certain patients may not be able to tolerate the stress of intra-abdominal surgery. It is, therefore, desirable to reduce the mortality and morbidity associated with intra-abdominal surgical intervention.

In recent years, methods have been developed to attempt to treat an abdominal aortic aneurysm without the attendant risks of intra-abdominal surgical intervention. Although techniques have been developed that may reduce the stress, morbidity, and risk of mortality associated with surgical intervention to repair aortic aneurysms, none of the prior art systems that have been developed effectively treat the aneurysm and exclude the affected section of aorta from the pressures and stresses associated with circulation. None of the devices disclosed in the references provide a reliable and quick means to reinforce an aneurysmal artery. In addition, all of the prior references require a sufficiently large section of healthy aorta abutting the aneurysm to ensure attachment of the graft. The proximal aortic neck (i.e., above the aneurysm) is usually sufficient to support a graft's attachment means. However, when an aneurysm is located near the iliac arteries, there may be an ill-defined neck or no neck below the aneurysm. Such an ill-defined neck would have an insufficient amount of healthy aortic tissue to which to successfully attach a graft. Furthermore, much of the abdominal aortic wall may be calcified making it extremely difficult to attach a graft thereto.

There are a number of shortcomings with the presently available graft products and their fixation within the abdominal aorta. Although sizing of "tube" or "bifurcated" grafts is radiographically assessed prior to surgery, it is necessary for the surgeon to have a large selection of graft lengths and diameters on hand to ensure an appropriate surgical outcome. Additional shortcomings include the placement of a "circular" profile graft with an associated fixation device within an essentially "ovoid" profiled vessel and the use of attachment means which fasten only to the insubstantial, structurally compromised (diseased) intima and media layers (i.e., strata) of the vessel wall. Research has shown yet another problem which indicates that the necks of the post-surgical aorta increase in size for approximately twelve months, regardless of whether the aneurysm experiences dimensional change. This phenomenon can result in peri-graft leaks and graft migration.

Graft migration is a significant problem affecting many of the grafts available within the intraluminal abdominal aortic aneurysm market. These grafts are attached within the aortic lumen at a proximal positioning by means of stents, which provide outward radial forces thereby forcing the graft into the lumen wall. In some instances barbs, part of the stent fabrication, provide additional fixation. There are numerous problems with this design approach. The stent of the aforementioned concept is expanded into a compromised vessel having questionable mechanical integrity. Second, the proximal distal neck has been shown to expand immediately post operatively and for a period of twelve months thereafter causing the graft to detach from or loosen with respect to the lumen. Finally, the barbs of the stent product are of questionable merit as they fasten into the intima of the lumen wall which has compromised mechanical integrity.

By comparison, the present inventors developed a graft assembly disclosed in U.S. patent application Ser. No. 08/896,415, filed Jul. 18, 1997, entitled "Method and Apparatus for the Surgical Repair of Aneurysms," the disclosure of which is incorporated herein by reference, that is positively fastened to the adventia, the outermost of three strata within the vessel wall, having appropriate mechanical integrity. The grafts disclosed in U.S. patent application Ser. No. 08/896,415 are not comprised by expansion of the distal neck. The present invention addresses the short comings of the prior art grafts. The present invention also enhances the performance of the graft assembly disclosed in U.S. patent application Ser. No. 08/896,415.

OBJECTS OF THE INVENTION

It is an object of the present invention to provide a temporary stent assembly for use during a surgical procedure.

It is another object of the present invention to provide a temporary stent assembly that can be selectively positioned within a vessel to temporarily secure a surgical component in place during a surgical procedure.

It is another object of the present invention to provide a stent assembly for use in a surgical procedure that can be advanced through a vessel and extended to secure a surgical component in place while the surgical component is being permanently secured to a vessel wall.

It is another object of the present invention to provide a stent assembly that is capable of holding a graft assembly against the aortic neck such that the graft assembly can be fastened to avoid leakage.

SUMMARY OF THE INVENTION

The present invention is directed to a stent assembly for use in temporarily securing a surgical component during a surgical procedure. The stent assembly includes a catheter assembly having at least one primary passageway extending there through. The stent assembly further includes a securing assembly defining a surface for exerting a force against an inner surface of the surgical component for temporarily securing the surgical component during the surgical procedure. The securing assembly includes a portion that extends through the at least one primary passageway. The catheter assembly may include a secondary passageway. The secondary passageway is adapted to receive a guide device therein. The securing assembly has a retracted position and an extended position. The securing assembly exerts a force against the surgical component while the securing means is in the extended position. The securing assembly may contain a coating which increases the gripping force of the securing assembly.

The stent assembly may be advanced through a vessel in order to selectively position the stent assembly with the securing assembly in the retracted position. The stent assembly may be inserted into the vessel via an axillary incision, a brachial incision, or a femoral or a common iliac arteriotomy, and may be used in the repair of an aneurysm.

According to an embodiment of the present invention, the stent assembly may be used to hold a surgical component against a vessel wall, wherein the surgical component may be fastened to the vessel wall to avoid leakage.

According to an embodiment of the present invention, the stent assembly may comprise a catheter assembly having a first primary passageway and a second primary passageway extending there through and a securing means for exerting a force against the surgical component for temporarily securing the surgical component during the surgical procedure, wherein the securing means includes a portion that extends through the first primary passageway and the second primary passageway. The first primary pasasgeway and the second primary passageway may be located adjacent to one another.

It is to be understood that both the foregoing general description and the following detailed description are exemplary and explanatory only, and are not restrictive of the invention, as claimed. The accompanying drawings, which are incorporated herein by reference, and which constitute a part of this specification, illustrate certain embodiments of the invention, and together with the detailed description serve to explain the principles of the present invention.

BRIEF DESCRIPTION OF THE DRAWINGS

The invention will be described in conjunction with the following drawing in which like reference numerals designate like elements and wherein:

FIG. 2 is a schematic view of the temporary stent assembly of FIG. 1 in a retracted position;

FIG. 3 is cross section of a temporary stent assembly in accordance with an embodiment of the present invention;

FIG. 4 is a schematic view of a temporary stent assembly in accordance with another embodiment of the present invention in an extended position;

DETAILED DESCRIPTION OF PREFERRED EMBODIMENTS

Figure 1:
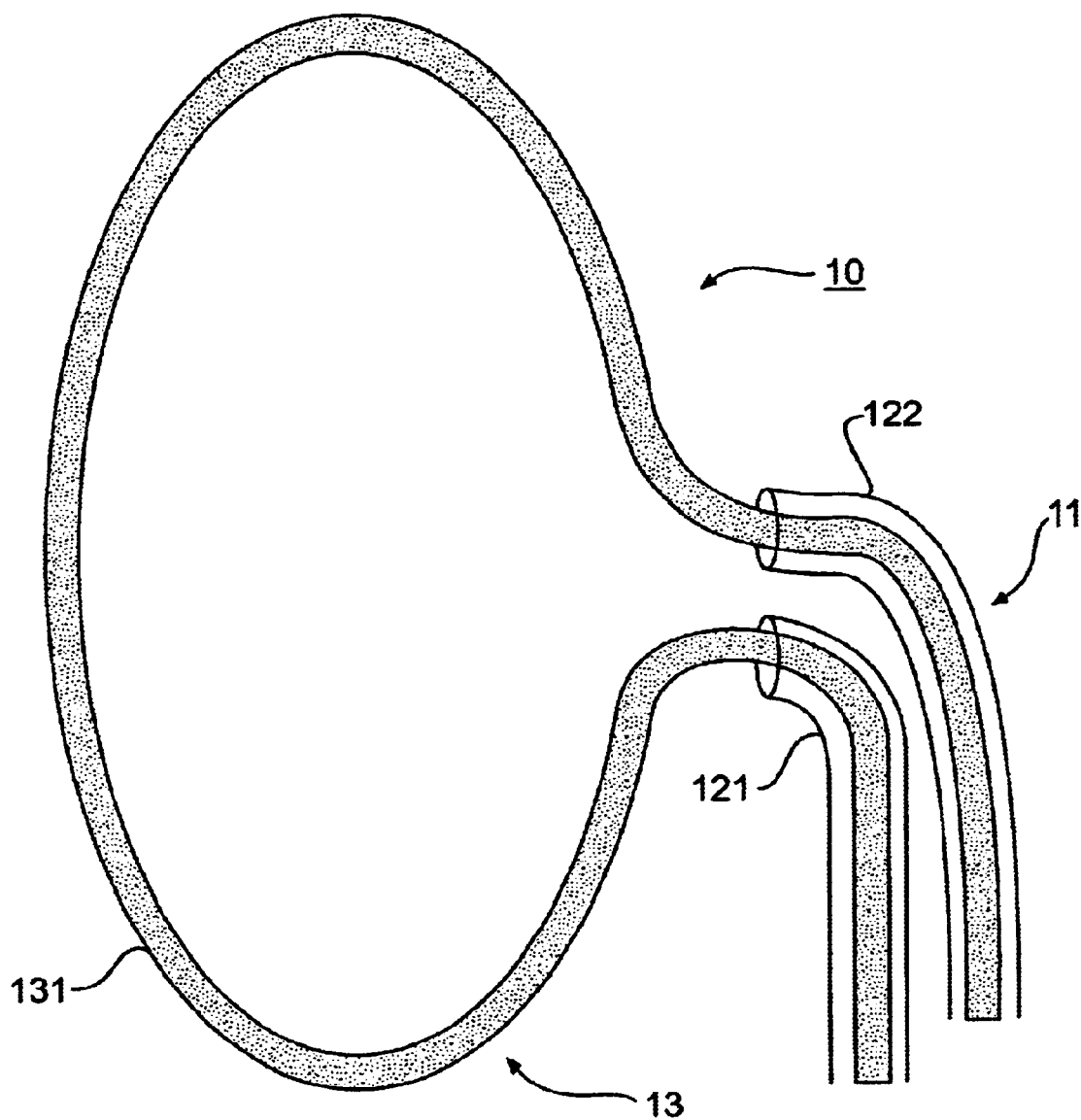
FIG. 1 is a schematic view of a temporary stent assembly in accordance with an embodiment of the present invention in an extended position.
Figure 5:
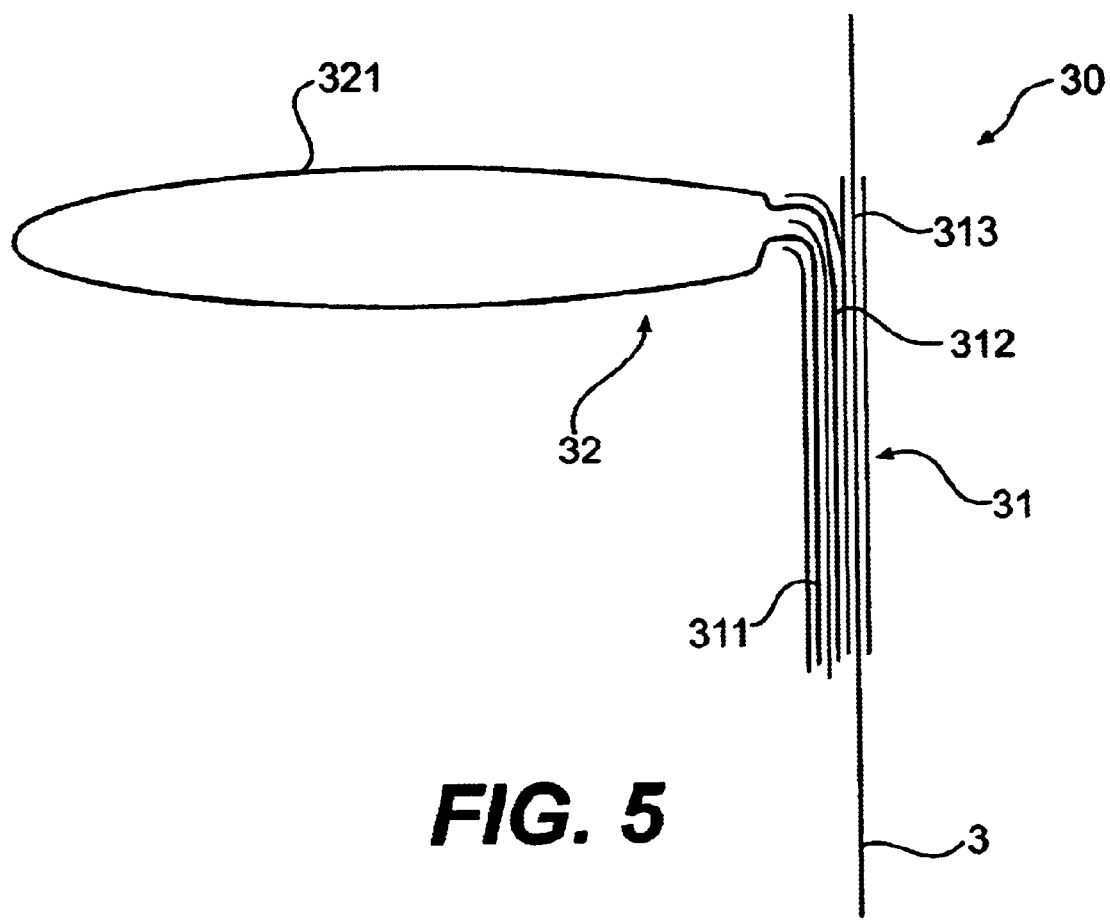
FIG. 5 is a schematic view of a temporary stent assembly in accordance with another embodiment of the present invention in an extended position.
Figure 6:
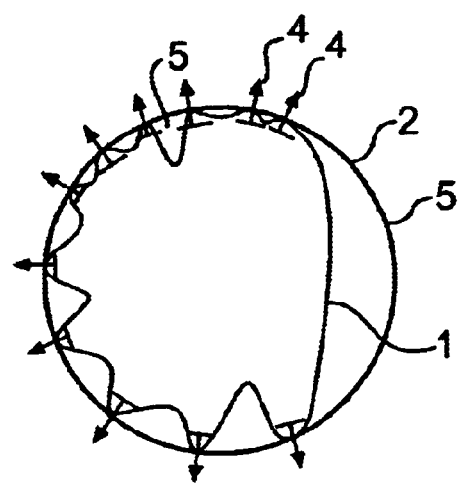
FIG. 6 is a schematic view of a graft assembly within a vessel.

A temporary stent assembly 10 in accordance with a first embodiment of the present invention will be described in connection with FIGS. 1, 2 and 3. The temporary stent assembly 10 is used to temporarily secure a surgical component 1, such as for example, a graft assembly for use in the repair of aneurysm. The stent assembly 10 includes a catheter assembly 11 having a first primary passageway 121 extending there through. A second primary passageway 122 extends through the catheter assembly 11 and is located adjacent the first primary passageway 121, as shown in FIG. 3. The catheter assembly 11 of the stent assembly 10 has sufficient length such that the catheter assembly 11 may be inserted into a vessel 2 to the desired location via either an axillary incision, a brachial incision or a femoral or common iliac arteriotomy.

A securing assembly 13 extends through the first and second primary passageways 121 and 122. A force exerting portion 131 of the securing assembly 13 extends from free end portions of the first and second primary passageways 121 and 122 located within the vessel 2. The securing assembly 13 has a retracted position, as shown in FIG. 2, wherein the force exerting portion 131 is located primarily within the first and second primary passageways 121 and 122. In the retracted position, the stent assembly 10 may be easily advanced and positioned within the vessel 2. Once located in the desired location, the securing assembly 13 is advanced such that the force exerting portion 131 is in an extended position such that the force exerting member 131 exerts a force against a surgical component 1 located within the vessel 2 to temporarily secure the component 1 within the vessel 2 against movement.

The securing assembly 13 may be manipulated between the extended position, as shown in FIG. 1., and the retracted position, as shown in FIG. 2, by operating the free ends of the securing assembly 13, not shown, which are located outside of the patient for easy operation and manipulation by a surgeon. It is also contemplated that the securing assembly 13 may be connected to a hand controller. The securing assembly 13 is preferably formed from stiff wire material such that it can exert sufficient force against the surgical component 1 when in an extended position.

The catheter assembly 11 preferably includes a third passageway 13, as shown in FIG. 3. A surgical guide line assembly 3, as disclosed for example in U.S. Provisional Application Nos. 60/118,779, filed Feb. 5, 1999, and 60/137,702, filed Jun. 7, 1999 and PCT International Patent Application No. PCT/US00/03871, entitled "SURGICAL GUIDE LINE ASSEMBLY AND SEPARATOR ASSEMBLY FOR USE DURING A SURGICAL PROCEDURE," filed on Feb. 4, 2000, the disclosures of which are incorporated specifically herein by reference. The surgical guide line assembly 3 controls the ease and manner in which the stent assembly 10 is advanced and a manipulated within the vessel 2.

FIG. 4 discloses a temporary stent assembly 20 in accordance with another embodiment of the present invention. The stent assembly 20 differs from the stent assembly 10 in that the first and second primary passageways 121 and 122 have been combined into a single passageway 210 within a catheter assembly 21. Although it is not depicted, it is contemplated that the stent assembly 20 may include an additional passageway through which a surgical guide line assembly 3 may extend. It is further contemplated that the stent assemblies 10 and 20 may be provided with additional passageways through which additional devices related to the surgical procedure may be inserted.

The securing assembly 22 of the stent assembly 20 also includes a force exerting portion 221 that is configured to conform to the interior of the vessel 2 when in an extended position to press the surgical component 1 against the vessel 2. The securing assembly 22 acts to apply a force against the surgical component 1 such that the component 1 can be properly and uniformly secured to the vessel to avoid leaks. In this manner, the gaps 5 between the component 1 and the vessel 2 adjacent the fasteners 4 can be avoided, thereby reducing risks associated with leakage.

FIGS. 5, 7, 8 and 9 illustrate a temporary stent assembly 30 in accordance with a preferred embodiment of the present invention. The stent assembly 30 includes a catheter assembly 31 having a first primary passageway 311 and a second primary passageway 312 formed therein. The passageways 311 and 312 receive a securing assembly 32, as described above in connection with assemblies 10 and 20. The stent assembly 30 further includes a third passageway 313 for receiving a surgical guide line 3.

Figure 7:
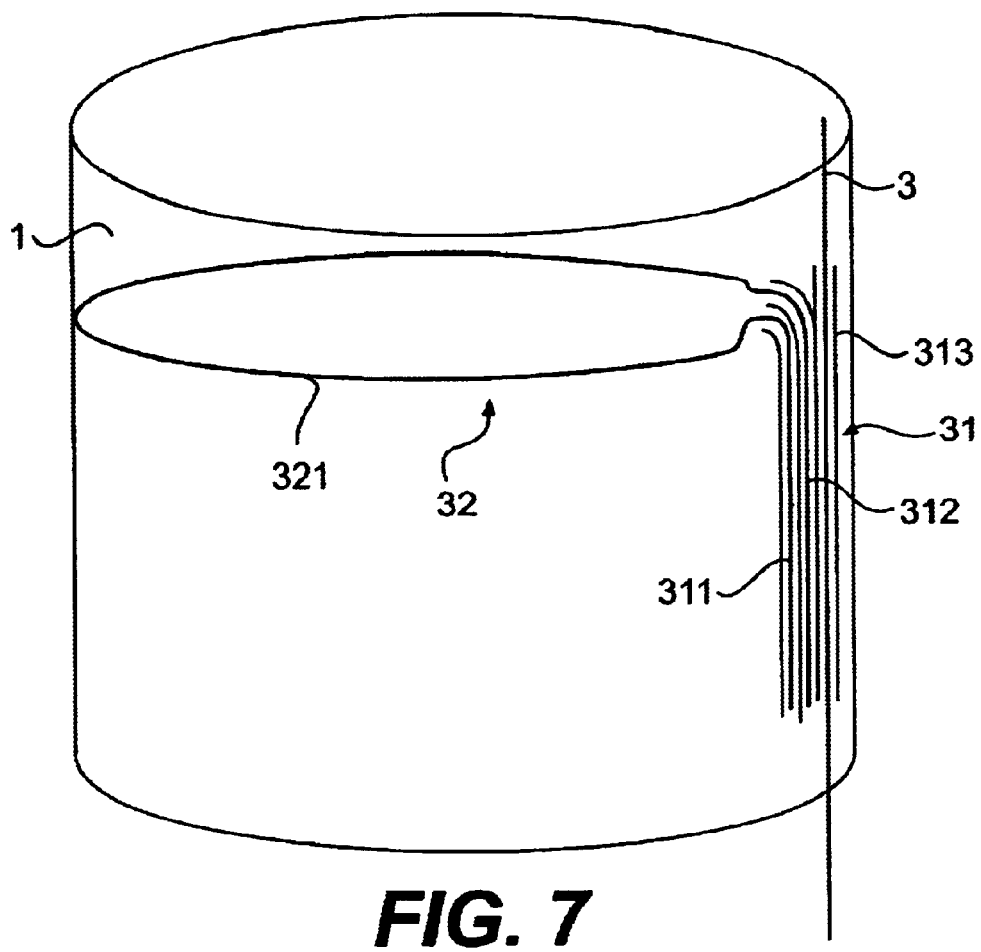
FIG. 7 is a schematic view of the temporary stent assembly of FIG. 5 in an extended position within a graft assembly.
Figure 8:
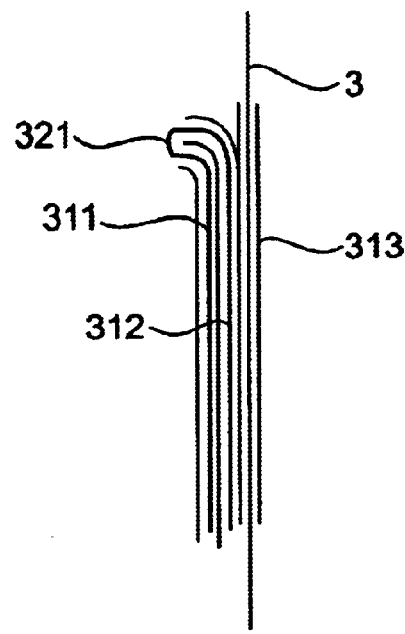
FIG. 8 is a schematic view of the temporary stent assembly of FIGS. 5 and 7 in a retracted position.

FIG. 7 illustrates the stent assembly 30 in an extended position for use in temporarily securing the graft assembly to a vessel 2 using surgical fasteners, as disclosed for example in U.S. Provisional Application No. 60/181,230, filed on Feb. 9, 2000, entitled "SURGICAL FASTENER," which is a continuation-in-part of U.S. patent application Ser. No. 09/442,768, filed Nov. 18, 1999, which is a continuation-in-part of U.S. patent application Ser. No. 09/213,233, filed Dec. 17, 1998, now U.S. Pat. No. 5,997,556, which is a continuation-in-part of U.S. patent application Ser. No. 08/958,524, filed Oct. 27, 1997, now U.S. Pat. No. 5,957,940, which is a continuation-in-part of U.S. patent application Ser. No. 08/896,415, filed Jul. 18, 1997, now U.S. Pat. No. 5,944,750, which claims priority to U.S. Provisional Patent Application No. 60/051,209, filed Jun. 30, 1997. The disclosures of which are specifically incorporated herein by reference. FIG. 8 illustrates the stent assembly 30 in a retracted position such that the stent assembly 30 may be inserted and manipulated in the vessel 2.

Figure 9:
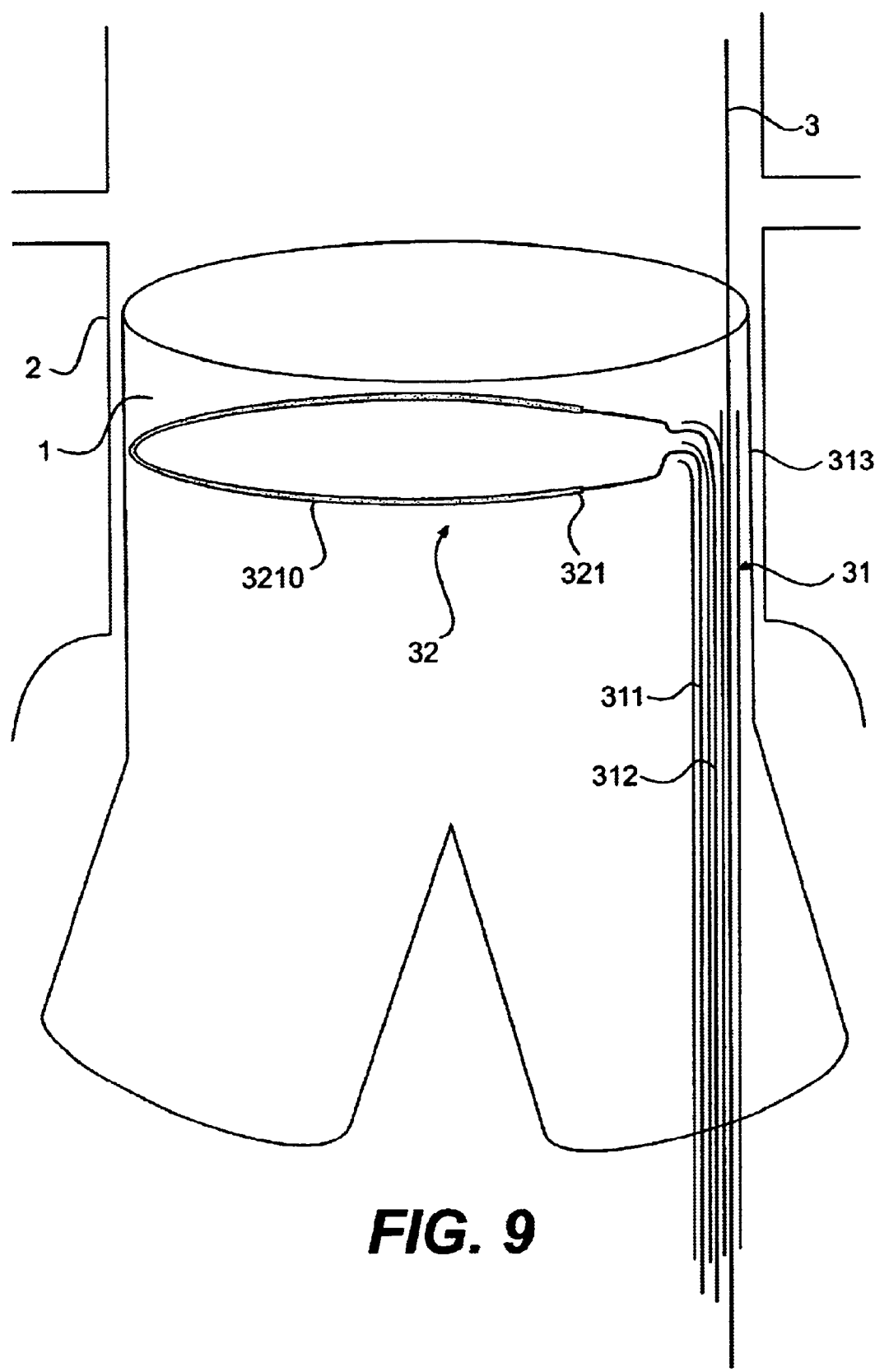
FIG. 9 is schematic view of the temporary stent assembly of FIGS. 5, 7 and 8 in an extended position within a graft assembly within a vessel.

FIG. 9 illustrates the stent assembly 30 in use within the vessel 2. The force exerting portion 321 of the securing assembly 32 includes a coating 3210, as shown in FIG. 9. The coating 3210 increases the gripping force of the securing assembly 32 by frictionally engaging the surgical component 1. This prevents undesired shifting of the surgical component 1 within the vessel 2 as it is being permanently secured to vessel using the above-identified fasteners.

It will be apparent to those skilled in the arts that various modifications and variations can be made in the construction and configuration of the present invention, without departing from the scope or spirit of the invention. While this invention have been described in connection with securing a graft assembly to a vessel wall, it is contemplated that it can be used in connection with any surgical procedure in which at least two components are secured together, such as, for example, securing a vessel to another vessel, or securing tissue to a vessel. It is intended that the present invention cover the modifications and variations of the invention, provided they come within the scope of the appended claims and their equivalence.

What is claimed is:

1. A stent assembly for use in temporarily securing a surgical component during a surgical procedure, said stent assembly comprising:
   a catheter assembly having at least one primary passageway extending there through; and
   securing means having at least two substantially free ends and a surface adapted to exert a force against an inner surface the surgical component for temporarily securing the surgical component during the surgical procedure, wherein said securing means includes a portion that extends through said at least one primary passageway.

2. The stent assembly according to claim 1, wherein said catheter assembly includes at least one secondary passageway, wherein said secondary passageway is adapted to receive a guide device therein.

3. The stent assembly according to claim 1, wherein said securing means has a retracted position and an extended position.

4. The stent assembly according to claim 1, wherein said stent assembly may be advanced through a vessel in order to selectively position said stent assembly.

5. The stent assembly according to claim 4, wherein said stent assembly is advanced through the vessel in order to selectively position said stent assembly while said securing means is in a retracted position.

6. The stent assembly according to claim 4, wherein said stent assembly is inserted into the vessel via an axillary incision, a brachial incision, or a femoral or a common iliac arteriotomy.

7. The stent assembly according to claim 3, wherein said securing means exerts a force against said surgical component while said securing means is in said extended position.

8. The stent assembly according to claim 1, wherein said stent assembly is used in the repair of an aneurysm.

9. The stent assembly according to claim 1, wherein said stent assembly is used to hold a surgical component against a vessel wall, wherein the surgical component may be fastened to the vessel wall to avoid leakage.

10. The stent assembly according to claim 1, wherein said securing means for exerting a force against said surgical component during said surgical procedure further comprises a coating which increases a gripping force of said securing means.

11. A stent assembly for use in temporarily securing a surgical component during a surgical procedure, said stent assembly comprising:
  a catheter assembly having a first primary passageway and a second primary passageway extending there through; and
  securing means for exerting a force against the surgical component for temporarily securing the surgical component during the surgical procedure, wherein said securing means extends through said first primary passageway and said secondary primary passageway.

12. The stent assembly according to claim 11, further comprising said securing means having at least two substantially free ends.

13. The stent assembly according to claim 11, wherein said securing means has a retracted position and an extended position.

14. The stent assembly according to claim 11, wherein said stent assembly may be advanced through a vessel in order to selectively position said stent assembly.

15. The stent assembly according to claim 14, wherein said stent assembly is advanced through the vessel in order to selectively position said stent assembly while said securing means is in a retracted position.

16. The stent assembly according to claim 14, wherein said stent assembly is inserted into the vessel via an axillary incision, a brachial incision, or a femoral or a common iliac arteriotomy.

17. The stent assembly according to claim 13, wherein said securing means exerts a force against said surgical component while said securing means is in said extended position.

18. The stent assembly according to claim 11, wherein said first primary passageway and said second primary passageway are located adjacent to one another.

19. The stent assembly according to claim 11, wherein said stent assembly is used to hold a surgical component against a vessel wall, wherein the surgical component may be fastened to the vessel wall to avoid leakage.

20. The stent assembly according to claim 11, wherein said securing means for exerting a force against said surgical component during said surgical procedure further comprises a coating which increases a gripping force of said securing means.

* * * * *